United States Patent [19]
Ruth et al.

[11] Patent Number: 4,746,211
[45] Date of Patent: May 24, 1988

[54] REAL TIME VELOCITY DETERMINATION

[75] Inventors: Bernhard Ruth, Echingen-Dietersheim; Diether Haina, Alsbach; Wilhelm Waidelich, München, all of Fed. Rep. of Germany

[73] Assignee: Gesellschaft für Strahlen- und Unweltforschung mbH, München, Fed. Rep. of Germany

[21] Appl. No.: 692,923

[22] Filed: Jan. 17, 1985

[30] Foreign Application Priority Data

Jan. 18, 1984 [DE] Fed. Rep. of Germany ....... 3401535

[51] Int. Cl.$^4$ ............................ G01P 3/36; A61B 5/02
[52] U.S. Cl. .................................... 356/28.5; 128/691
[58] Field of Search .................. 356/28, 28.5; 128/691

[56] References Cited

U.S. PATENT DOCUMENTS

| | | | |
|---|---|---|---|
| 3,432,237 | 3/1969 | Flower et al. | 356/28.5 |
| 3,525,569 | 8/1970 | Gamertsfelder et al. | 356/28.5 |
| 4,109,647 | 8/1978 | Stern et al. | 128/666 |
| 4,311,383 | 1/1982 | Ohtsubo | 356/28 X |
| 4,476,875 | 10/1984 | Nilsson et al. | 356/28.5 X |

FOREIGN PATENT DOCUMENTS 3242771 5/1984 Fed. Rep. of Germany .

OTHER PUBLICATIONS

G. Stavis, "Optical Diffraction Velocimeter," Instruments and Control Systems, Feb. '66, pp. 99–102.
Takai et al, "Real-time velocity measurement for a diffuse object using zero-crossings of laserspeckle," J. Opt. Soc. Am, Apr. 1980, pp. 450–455.
Ogiwara et al, "A speckle pattern velocimeter using a periodical differential detector," *Japanese Journal of Applied Physics*, vol. 14, 1975, pp. 307–310.
Ohtsubo et al, "Velocity measurement of a diffuse object using time-varying speckles," *Optical and Quantum Electronics*, Nov. 1976, pp. 523–529.
Nishihara et al, "Optical-fiber laser Doppler velocimeter for high resolution measurement of pulsatile blood flows," *Applied Optics*, May 15 1982, pp. 1785–1790.
Pusey, J, Journal of Physics D: Applied Physics, "Photon correlation study of laser speckle produced by a moving rough surface," vol. 9, pp. 1399–1409.
Ohtsubo, J. and T. Asakura, Optical and Quantum Electronics 8, "Velocity measurement of a diffuse object by using time-varying speckles, 1976, pp. 523–529.

*Primary Examiner*—Stephen C. Buczinski
*Assistant Examiner*—Linda J. Wallace
*Attorney, Agent, or Firm*—Spencer & Frank

[57] ABSTRACT

Method and apparatus for determining the velocity of an object in a given direction without contacting the object, by: directing coherent radiation to the object in a direction substantially perpendicular to the given direction to cause radiation to be scattered from the object to produce a speckle pattern exhibiting a speckle spectrum, the speckle pattern at a location spaced from the object having a time dependency which is a function of movement of the object, detecting the speckle pattern intensity at the location spaced from the object, producing a first signal representative of the detected speckle intensity, and producing, from the first signal, a time-dependent intensity signal having a value which is weighted as a function of the frequency of the first signal.

7 Claims, 1 Drawing Sheet

REAL TIME VELOCITY DETERMINATION

BACKGROUND OF THE INVENTION

The present invention relates to a method, a circuit arrangement and an apparatus for a non-contacting real time determination of velocities of one or a plurality of movements at an object in a direction perpendicular to a coherent radiation impinging on the object, with the scattered light of the coherent radiation producing a spatial speckle pattern over a speckle spectrum, and with the speckle pattern becoming time dependent due to the movements at the object.

If a laser beam of wavelength $\lambda$ impinges on an object in the x direction, and the average distance $\Delta x$ between scatter centers is $>>\lambda$, the scattered light forms a granular structure, called speckles. This is the case, for example, on all normal surfaces. The intensity distribution of the speckles is irregular. Certain mathematical interrelationships exist for the statistic distribution of the speckles. These mathematical interrelationships do not depend on the characteristics of the object, as long as the requirement of $\Delta x>>\lambda$ is met.

With the laser at rest and the object at rest, the speckle pattern is stationary. Under certain conditions of mutual position of laser, object and observation point, the speckle pattern moves as a whole if the object itself moves. This results in a specific speckle velocity $V_s$ which, in suitable cases, is proportional to the velocity of the object. One way to record speckle movement is to measure the light intensity of the scattered light on an effective detector surface which is small compared to the average speckle size $\sigma$.

Such a detector produces a signal I proportional to the light intensity on its surface and there now exist various ways to determine the speckle velocity from the time-dependent form, I(t), of that signal. One of these methods is the so-called correlation method. Here, the incident light intensities are detected at two spatially separate locations and the resulting intensity signals are recorded. Two time dependencies result for the intensity. Both intensity time dependencies are stored. The correlation function calculated therefrom has a peak from whose position the speckle velocity can be determined.

The drawback of this method is that it requires a large amount of electronic equipment and that the velocity is not determined in real time (Pusey, J. Phys. D 9 (1976) page 1399). In principle, this method does not utilize any specific speckle characteristic.

Only a single time dependent signal I(t) is required for the method employing time integration of the signal I(t). Initially, average values $N_i$ are formed from the speckle intensity signal I(t) by way of integration over a succession of time intervals, with a computer calculating the standard deviation S and an overall average $\overline{N}$. The quotient of both values, $S/\overline{N}$, is a non-linear measure for the speckle velocity. The drawback of this method is again the high costs for the electronic computer and the fact that it is not a real-time method. In principle, the fact that the contrast of the speckle signal is known to go toward zero with increasing integration time, is utilized here (J. Ohtsubo, T. Asakura, Opt. Quant. Electr. 8 (1976) 523).

An earlier patent application, in the Federal Republic of Germany, No. P 3,242,771.9, discloses the so-called speckle counting process. This method counts the points of intersection between the intensity signal I(t) and a threshold level S. The threshold level S is set to be proportional to the average intensity value $\overline{I}$. The advantage of this method is that the costs for electronic equipment are reduced and the method has real-time characteristics.

However, the drawback of this method is that noise is superposed on the speckle signal. Particularly at low velocities, this noise results in erroneous measurements because the velocity indicated is too high. In principle, this method utilizes the speckle characteristic that the time interval $\Delta t$ between two counts has an average $\Delta t$ which is given by $\overline{\Delta t}$ being approximately const$\cdot\sigma/V$. None of the prior art methods is suitable to separate superposed velocities.

SUMMARY OF THE INVENTION

It is an object of the present invention to record the movement of a speckle pattern in such a manner that the resulting data permit a determination of the speckle velocity independently of other superposed velocities. In particular, it is an object of the invention to determine the blood circulation velocity near the skin surface or in other parts of the human body.

The above and other objects are achieved, according to the invention, by a method and apparatus for determining the velocity of an object in a given direction without contacting the object, by directing coherent radiation to the object in a direction substantially perpendicular to the given direction to cause radiation to be scattered from the object to produce a speckle pattern exhibiting a speckle spectrum, the speckle pattern at a location spaced from the object having a time dependency which is a function of movement of the object, detecting the speckle pattern intensity at the location spaced from the object, producing a first signal representative of the detected speckle intensity, and producing, from the first signal, a velocity-dependent intensity signal having a value which is weighted as a function of the frequency of the first signal.

The method according to the invention takes advantage of the fact that, for an object at rest, I(t)=constant and no frequencies unequal to 0 occur. If the object moves, then frequencies unequal to zero do occur. Thus, measuring the intensity of the signal, which is normally an electrical signal, at frequencies unequal to zero is a measure for the velocity $v_s$. The invention particularly utilizes the fact that the speckle pattern as a whole has a granular structure. If a change is made to not simply determine the intensity above a frequency $v_0$, but to first suitably modify the signal, then the intensity formation produces a measured value which is proportional to velocity $v_s$. This measure resides in that the amplitudes $A(v)$ of the spectrum must first be amplified by a factor which is proportional to $v$.

On the basis of the specific shape of the speckle spectrum, the intensity of the thus formed signal is proportional to velocity $v_s$. This proportionality has been proven by theoretical derivation and experimental data.

Due to the intensity formation, measured value P is also proportional to the average intensity $\overline{I}$ at the point of observation. To avoid interference resulting from laser output intensity fluctuations and changes in reflection conditions, such interference can be eliminated by dividing the measured value by the average light intensity $\overline{I}$.

The advantage of the method is that the cost of the required electronic equipment can be kept low. The frequency dependent weighting is effected by time differentiation and the intensity formation by a power meter.

It is also not absolutely necessary to simultaneously measure the total intensity. In the worst case, the dependency is linear with variations in intensity. If thus great differences in velocity are to be measured and, on the other hand, a stable laser is available, this can be omitted.

In the above-described, previously proposed speckle counting method described in Federal Republic of Germany Application No. P 3,242,771.9, this is not the case. In that method, the counting rate is very sensitively dependent upon threshold S and thus on the measured average intensity $\bar{I}$.

An important condition for speckle formation is that the laser light is scattered at scatter centers which have an average distance $\Delta x \gg \lambda$. In normal moving objects, all scatter centers move at the same velocity. However, when observing blood flow near the skin surface of a living subject, the scatter centers may have different velocities. The resulting speckle pattern now moves under the influence of the velocity, $v_H$, of the skin surface and of the velocity, $v_B$, of the red blood cells. Since this is a coherent superposition of two speckle patterns according to the two velocities, a new speckle pattern is created which in appearance does not differ from the speckle pattern of a normal object. Only its behavior over time is different.

With the prior art speckle methods it is not possible to separate these two velocity components from one another or to separate even other such velocities. With these methods, the result would simply be that either a slightly higher velocity is indicated without it being possible to distinguish whether this was the result of increased skin velocity or increased movement of the blood. In any case, in no experiments was it possible to determine a difference between skin through which blood flowed and skin through which no blood flowed.

In the first-mentioned prior art methods, there probably exists no possibility at all to determine, in principle, a difference between skin through which blood flows and skin through which no blood flows. Even if this were possible, such a method could not be used in practice, because the measuring periods are very long and the amount of apparatus required would be too large.

Since the major portion of the light is scattered over the skin surface and the skin cells, the movement of the speckle pattern is also primarily determined by the skin velocity $v_H$. Only a small portion of the light penetrates into the blood vessels and is there scattered back to return back to the outside. Therefore, the proportion of blood movement in the respective speckle pattern is always low.

If a strip of textile were glued to the skin and then a measurement were made or the blood supply to one part of the skin were suppressed, an approximate measured value for the skin velocity would result. The spectrum of signal I(t) for such a measurement is composed of a superposition of a plurality of velocities. Measurement at the skin at a location where blood flow occurs produces a spectrum in which high frequencies are more prevalent compared to measurements made at skin through which no blood flows. This permits the conclusion that the average velocity $\bar{v}_B$ of the movement of blood is higher than the average velocity, $\bar{v}_H$, of the movement of skin.

Roughly, the spectrum can be composed of two parts: movement of the skin and movement of the blood. Due to the difference between the average velocities $\bar{v}_H$ and $\bar{v}_B$, it is now possible to separate the signal components associated with these two velocities. A signal amplitude representation is formed only of that portion of the spectrum signal whose frequency lies above $v_g$, and the portion with a frequency less than $v_g$ is suppressed. In the spectrum, this would correspond to integration over a frequency interval of $v_g$ to infinity.

In principle, the separation of the two velocity ranges is possible even with intensity formation of the electrical signal without the use of weighted amplification. The frequency dependent amplification increases the signal differences between skin through which blood flows and skin through which no blood flows.

There exists no uniform definition of blood flow. However, it is considered to be appropriate to set the blood flow to be proportional to the velocity and the quantity of the blood, respectively. Thus, the method permits a determination of blood flow since the signal is proportional to the velocity, because of the frequency dependent weighting and also proportional to the quantity of moving blood. If more moving blood enters into the area through which the laser light penetrates, the signal becomes larger of course.

DESCRIPTION OF THE PREFERRED EMBODIMENTS

Figure 1:
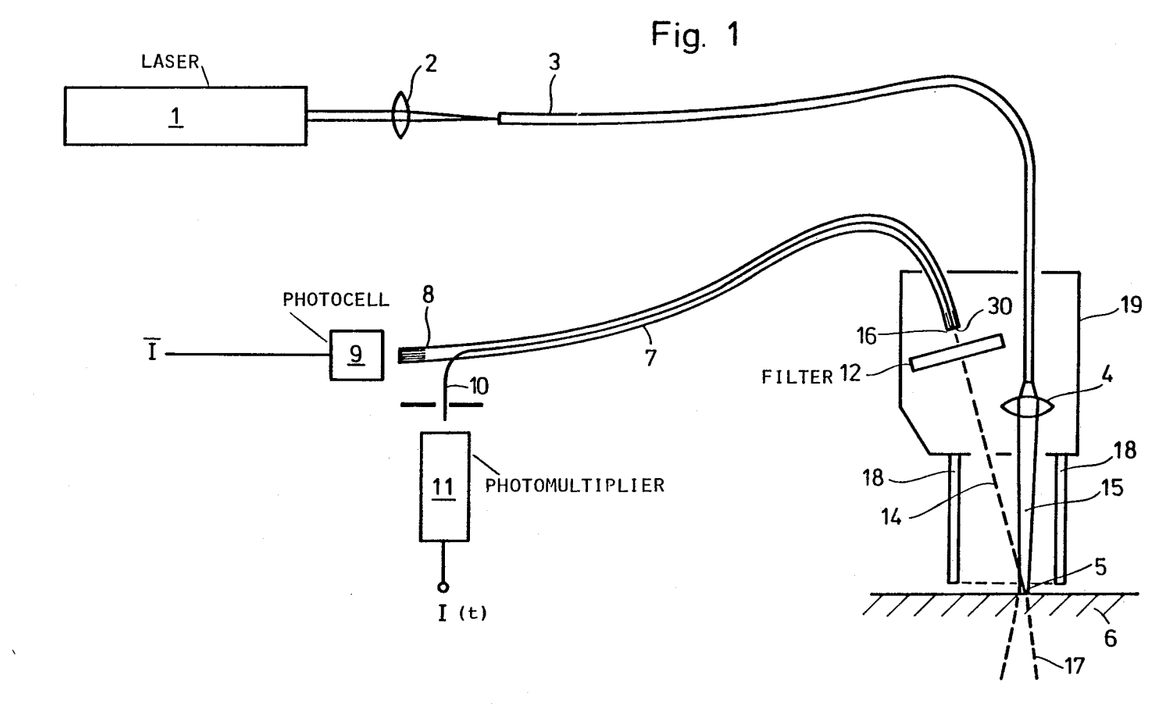
FIG. 1 is a simplified pictorial view of a measuring arrangement for carrying out the present invention.

FIG. 1 is a pictorial illustration of a measuring arrangement or device with which velocity can be determined. A laser beam 15 is directed to a measuring point 5 on an object 6. Due to the surface roughness of object 6, the light scattered therefrom forms a granular pattern, i.e. speckles, where the average size $\sigma$ of the speckles at the locus of observation 16 is determined only by the wavelength $\lambda$ of the light employed (e.g. He-Ne laser, $\lambda = 633$ nm), the size of the beam spot of beam 15 at point 5 and the distance from measuring point 5 to locus 16. With a suitable optical arrangement, the speckle pattern moves as a whole so that a speckle velocity $v_s$ can be defined.

For small angles between laser beam 15 and the optical axis 14 of the observation device there exists a simple relationship as described above.

The speckles are detected at an aperture 30 which, in order to substantially maintain the speckle contrast, is smaller than the average speckle size $\sigma$. In order to obtain a small angle between laser beam 15 and observation device optical axis 14, and to additionally assure flexible access to the desired measuring points, light conductors, or optical fibers, 7, 8, 10 are utilized. The beam from a laser 1 is focussed through a lens 2 into an optical fiber, or fiber bundle, 3. The exciting beam is highly divergent so that it is collimated by lens 4 to form beam 15 which is directed toward measuring point 5 on object 6.

The diameter, D, of the beam spot at measuring point 5 must be as small as possible so that the speckle size $\sigma$ reaches the maximum size required for detection. Yet, the distance between measuring point 5 and the locus of observation 16 must not be too large because then the available light intensity would not be sufficient for detection. On the other hand, the diameter D must not depend greatly on the distance between lens 4 and object 6 because then even a slight change in the distance would result in a great change in speckle size $\sigma$, which would again bring about an error in the velocity measurement. The beam profile must therefore have a long, narrow waist 17. This is brought about by carefully matching the divergence of the laser beam exiting from optical fiber 3, the focal length of lens 4 and the distance between lens 4 and the end of optical fiber 3. Thus the diameter of the beam 15 does not change considerably within e.g. a distance from 55 to 65 mm in front of the lens.

Fiber bundle 7 forms part of the detection system and starts at locus of observation 16, which is as close as possible to the end of light conductor 3 and to lens 4 to keep the angle small between the incident laser beam 15 and the direction of observation 14. To detect speckle movement and produce therefrom a time dependent speckle intensity signal I(t), a single fiber 10 of bundle 7 leads from locus 16 to a light detector 11. Since the effective diameter of the individual fiber 10 is the effective aperture 30 for the speckle detection, the distance between measuring point 5 and locus of observation 16 must be selected such that the speckle size $\sigma$ is somewhat larger than the diameter of fiber 10.

If the object 6 moves, the speckles move past the end of the individual fiber 10 so that light detector 11, e.g. a photomultiplier, at the end of the individual fiber 10 indicates time-dependent speckle intensity I(t). The individual fiber 10 is disposed in the center of the remaining fibers 8 of bundle 7. Fibers 8 form a bundle which leads to a further detector 9. Since fiber bundle 8 is composed of approximately 400 individual fibers each having a diameter equal to the speckle size $\sigma$, and since the light incident on those fibers is measured in a common detector 9, the signal produced by detector 9 represents the average speckle intensity $\bar{I}$ at the same location at which speckle intensity I is measured with the aid of detector 11. The quality of the average formation G is given by $$G \alpha \sqrt{N},$$

where

G is the standard deviation of the average values divided by the mean of the average values, N is the number of the optical fibers with a diameter equal to the speckle size 6, and $\alpha$ means proportional to.

A tubus 18 serves to maintain the optimum distance between measuring head 19 and object 6. A filter 12 permits only light at the laser wavelength to pass and thus reduces the noise on the input signals to detectors 9 and 11 caused by scattered light of other wavelengths. Measuring head 19 carries the output end of fiber 3, as well as lens 4, the fiber bundle at locus 16 and filter 12.

I(t) is thus the time-dependent signal of the speckle intensity whose spectrum is determined by the spatial spectrum of the speckle pattern and by the velocity of the object.

Prerequisite for use of the method according to the present invention is that the intensity I(t) be determined by means of a detector 11 whose effective measuring surface area is smaller than the average speckle size. The effective surface area may be defined by the detector itself, by a small aperture placed onto it or, as in the embodiment of FIG. 1, by the cross section of the associated light conductor.

In contrast to the speckle counting method, the velocity determination procedure is not sensitively dependent on the total intensity of the scattered light. Therefore, it is not necessary, in principle, to determine total intensity. If the total light intensity fluctuates by no more than 5%, the determined velocity also contains an error of 5%. But this possible error can also be compensated.

Simultaneous measurement of the laser light intensity and a mathematical division operation eliminates the influence of fluctuations in laser light intensity. Simultaneous measurement of the total intensity of the scattered light and division also eliminates the influence produced by changes in reflection from object 6.

Simultaneous measurement of the total intensity of the scattered light $\bar{I}$ at the same location as the determination of speckle intensity I also eliminates the influence of direction dependent scattering.

I and $\bar{I}$ can be determined in various ways, e.g. by means of a beam splitter or by means of a glass fiber arrangement as shown in FIG. 1. The benefit of the glass fiber arrangement is its good maneuverability, which is particularly important in connection with measurements on the skin.

If in a stationary speckle pattern, the speckle pattern is scanned by means of a small aperture 30, a locus dependency $I_r(y)$ results with a local spectrum.

r indicates that $I_r$ is a space dependent function.

y is a space coordinate.

The function $I_y(y)$ could be obtained by scanning the speckle pattern.

The local spectrum of the speckle pattern is generally known from the literature. If now the speckle pattern moves at a velocity V and is observed at one location, a time-dependent light intensity I(t) results behind the aperture at $I(t) = I_r(vt)$.

v is the velocity.

I is a time-dependent function.

To illustrate the occurrence in connection with the speckle pattern, let us observe a sine-shaped light intensity distribution which is brought past the aperture at a velocity $V_S$. The sine-shaped intensity has a locus dependency $$I_{i,r}(y) = I_0 \sin\left(2\pi \frac{y}{y_0}\right).$$

The corresponding time dependency is $$I_i(t) = I_0 \sin\left(2\pi \frac{vt}{y_0}\right).$$

Obviously a high velocity results in the occurrence of higher frequencies in both time-dependent functions. In these functions i indicates functions concerning the example with a sine-shaped light intensity, $I_o$ is the amplitude and $y_o$ is the wave length in space of the sine-shaped light intensity distribution.

In order to incorporate the velocity in the amplitude, a one-time time differentiation is made.

$$\dot{I}(t) = \frac{d}{dt} I_i(vt)$$

e.g. $\dot{I}_i(t) = 2\pi \frac{v}{y_o} I_o \cos\left(2\pi \frac{vt}{y_o}\right)$, where
v is the velocity (see above),
$y_o$ is the wavelength in space (see above).
Now the intensity of the signal $\dot{I}(t)$ is determined to obtain the velocity.

$$P(v) = \sqrt{\int |\dot{I}(t)|^2 dt}$$

P(v) is defined by this equation.

For the illustrated embodiment, the following calculations then apply:

$$P_i(v) = \sqrt{\int_0^\infty /2\pi \frac{v}{y_o} I_o \cos\left(2\pi \frac{vt}{y_o}\right)/^2 dt}$$

$$= \sqrt{\frac{1}{2}\left(2\pi \frac{v}{y_o} I_o\right)^2}$$

$$= \sqrt{2}\; \pi \frac{v}{y_o} I_o$$

($P_i(v)$ is the equivalent function to P(v), now applied for the example with the sine-shaped light intensity.

$$M_i(v) = \frac{P_i(v)}{I_o} = \sqrt{2}\; \pi \frac{v}{y_o} \text{ (the measured value)}$$

$M_i(v)$ is defined by the first equation. It follows that $M_i(v)$ is proportional to velocity v.

For the speckle pattern, the value P(v) can be calculated only as the statistical average because the local spectrum of the speckles is known.

According to one theorem (the Power theorem), the following applies:

$$\int /\dot{I}(t)/^2 dt = \int /\mathcal{F}(\dot{I}(t))/^2 dv$$

This is the square of the Fourier transform of I(t), the "power spectrum".

$\nu$ is the frequency.

$$\int /\dot{I}(t)/^2 dt$$

$$= \int /\mathcal{F}(\dot{I}(t))/^2 dv$$

$$= \int /\mathcal{F}\left(\frac{d}{dt} I_i(vt)\right)/^2 dv$$

$$= \int /2\pi i \frac{v}{\nu} \mathcal{F}(I_i(vt))/^2 dv$$

This is so because in the spectrum, time differentiation corresponds to a multiplication with the frequency. $1/v$ results from a type of substitution rule.

$$\int |\dot{I}(t)|^2 dt = 4\pi^2 \int v^2/\frac{1}{v} \mathcal{F}(I_i(vt))/^2 dv$$

This is the spectrum of the spatial speckle pattern known from literature. The expression is inserted to get the following equation.

$$\int |\dot{I}(t)|^2 dt = 4\pi^2 \int v^2 \left(\overline{I}^2\left(-\frac{\sigma^2}{v^2} v + \frac{\sigma}{v}\right)\right) dv$$

where $\overline{I}$ is the average intensity and $\sigma$ is the average speckle size.

$$= \frac{2}{3} \pi^2 I_o^2 \frac{v^2}{\sigma^2}$$

This results in:

$$P(v) = \sqrt{\frac{2}{3}}\; \pi I_o \frac{v}{\sigma}$$

$$M(v) = \sqrt{\frac{2}{3}}\; \pi \frac{v}{\sigma}$$

A comparison with the result of the sine-shaped intensity shows:

$$y_o \triangleq \sqrt{3}\sigma$$

Time averaging, i.e. the intensity determination, corresponds to integration of the spectrum. If two velocities are superposed, skilled selection of the frequency intervals makes it possible to effect a separation. The position of the frequency interval could be obtained by interpreting the spectra of the speckle intensity signal I(t). For example, measuring at the skin a separation of the blood flow velocity from other moving objects (body, skin, other cells . . . ) is achieved by selecting an interval from 50 Hz to 1500 Hz.

If now only given frequency intervals are utilized for the intensity formation, the velocity measurements are separated. A reduction to practice is realized in that the time-dependent signal is changed by means of active filters. It is known, for example, that a highpass filter suppresses the low frequencies and thus serves to detect high velocities. The same applies correspondingly for a lowpass filter and low velocities.

Figure 2:
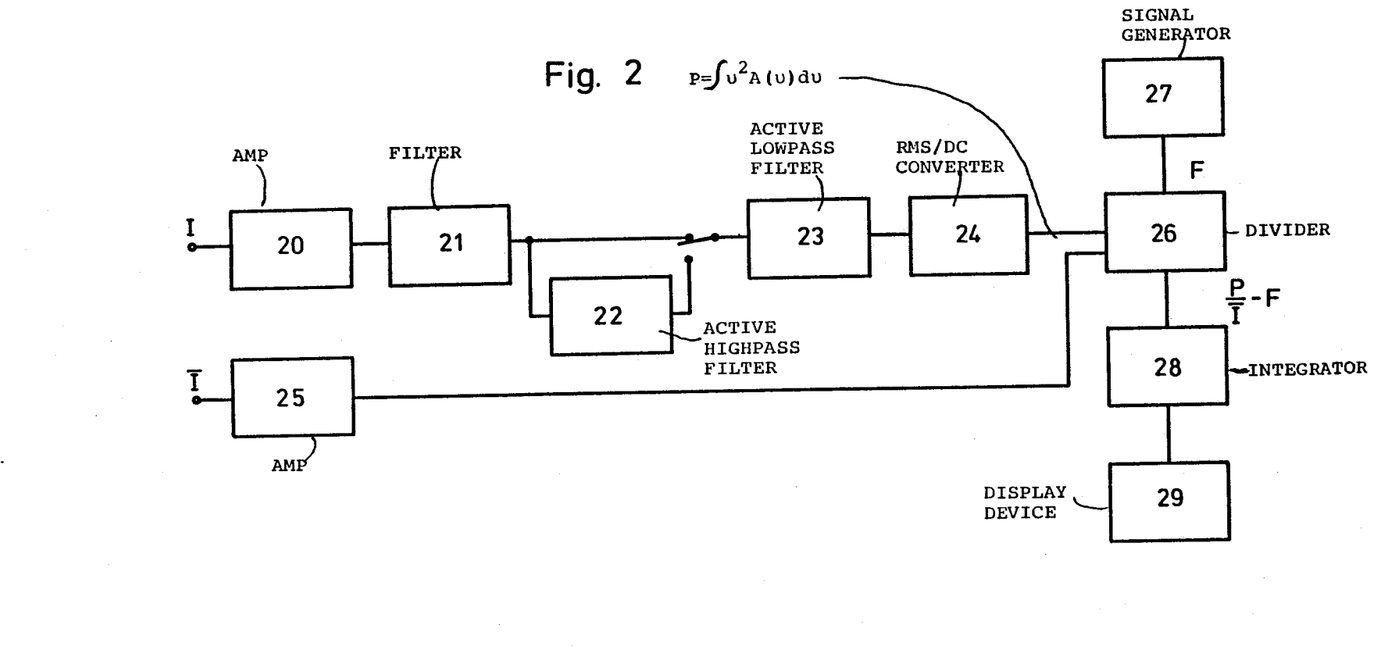
FIG. 2 is a block diagram of a circuit for producing velocity information according to the invention.

The measured value $M(v_s)$ can be realized by means of the electronic circuit shown in FIG. 2, with FIGS. 3a through 3h showing the functions of the individual components in the circuit arrangement.

The signal I(t) from detector 11 is amplified in amplifier 20. This signal has the time dependency shown in FIG. 3a and the spectrum $A(\nu)$ shown in FIG. 3b. The signal from amplifier 20 passes through a linear filter 21 or a differentiating member, respectively, in which it is amplified proportionally to frequency $\nu$ by means of an adjustable proportionality constant, producing the output signal and spectrum shown in FIGS. 3c and 3d. The simplest way to realize this is in the form of an RC member as a passive component. Higher demands for linearity and dynamics can be met by an active circuit.

Figure 3:
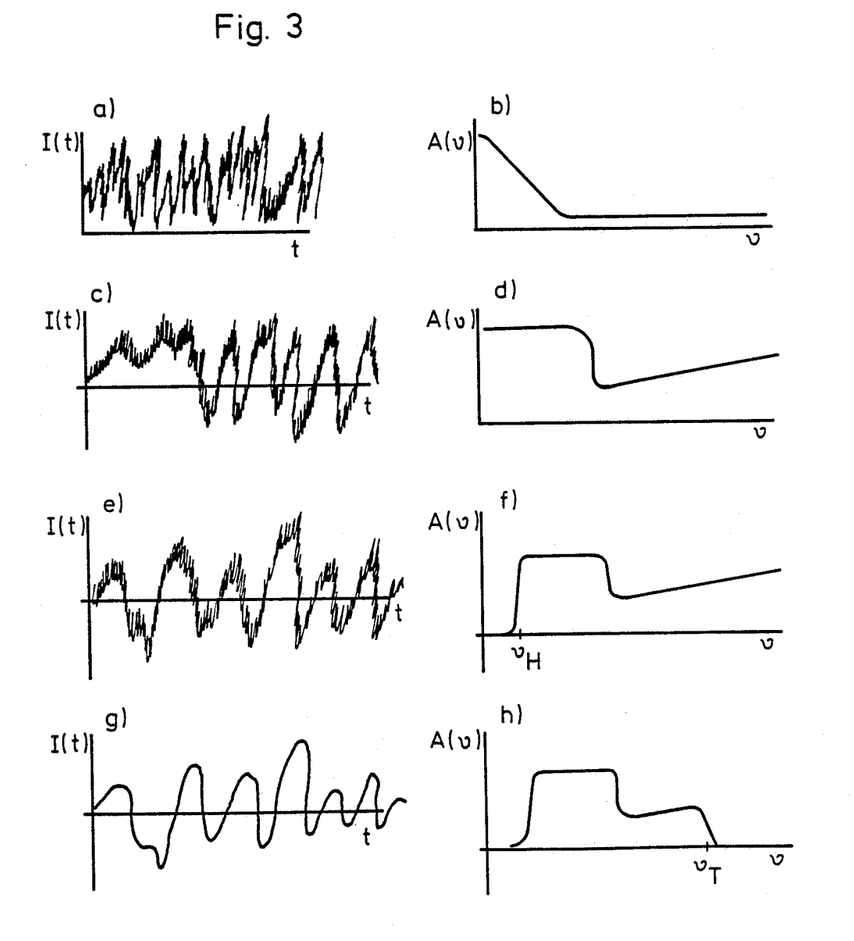
FIGS. 3a through 3h are waveform diagrams illustrating the operation of the circuit of FIG. 2, FIGS. 3a, c, e and g being signal vs. time waveforms and FIGS. 3b, d, f and h being frequency spectrum diagrams.

Noise from photomultiplier and laser are superposed on the speckle signal. Active lowpass filter 23 serves to constrict the observed frequency range, e.g. to a limit frequency $v_T$, without adversely affecting linearity, if limit frequency $v_T$ is greater than the maximum frequency of I which is fixed by speckle size $\sigma$ and the maximum velocity. The output signal of lowpass filter 23 and related spectrum are shown in FIGS. 3g and 3h.

In practice, an RMS power/DC converter 24 performs an integration and determines the total intensity, P, of the time-dependent signal. In principle, the integration is a "specific" integration over time of the time-dependent signal. However, it is mire clearly seen in the spectrum in which a frequency integration is effected over a certain frequency interval. The value of the integrated signal from converter 24 is mathematically divided in divider 26 by an average intensity signal $\bar{I}$ which is derived from detector 9 and amplified in amplifier 25. The result of this division then represents the measured value $M(v_S)$. After time integration in integrator 28, which determines the accuracy of the measurement, $M(v_S)$ is displayed in display device 29.

The noise from photomultiplier nd laser does of course also occur in the frequency range under observation. This share of measured signal $M(v_s)$ can be eliminated by generating a fixed, settable signal value F in a signal generator 27 and subtracting value F from the quotient of $P/\bar{I}$.

Since the influence of the blood flow movement is best determined in the higher frequency portion, the average velocity of inadvertent body movement is less than that of the movement of the blood. This difference is utilized for the separation of the two velocities. An active highpass filter 22 whose output signal and spectrum, respectively, are shown for limit frequency $v_H$ in FIGS. 3e and 3f, is connected into the circuit for this purpose. On the one hand, this filter 22 must sharply separate the two velocity ranges, i.e., it must have a sharp edge. On the other hand, in order to maintain linearity, it must be frequency independent for frequencies above $v_H$. For example, the filter 22 may be given by a 4-pole Butterworth filter with a cut-off-frequency at 50 Hz.

Figure 4:
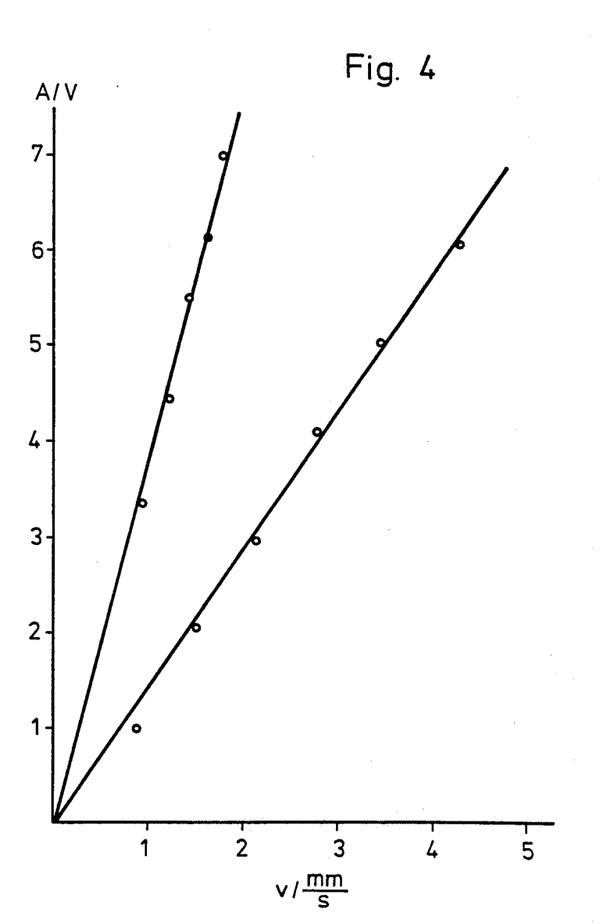
FIGS. 4–6 are diagrams illustrating the measurement results achieved with the invention.

If the plane of observation varies by $\pm 5$ mm from its nominal position, no change appears in the velocity signal in the circuit arrangement or apparatus according to FIG. 1. The linearity achieved with the method according to the invention is shown in FIG. 4. Deviations at slower velocities are the result of the beam spot not being square as in the theoretical derivation but having an $e^{-x^2}$ profile and the speckle movement being measured by means of an aperture which is not negligibly small compared to the speckle size.

In FIG. 4 the circles are measuring values A (in Volts) by the equipment at different velocities of a test object. The different sensitivities indicated by the slope of the two lines are achieved by applying speckle patterns of different speckle size 6.

Figure 5:
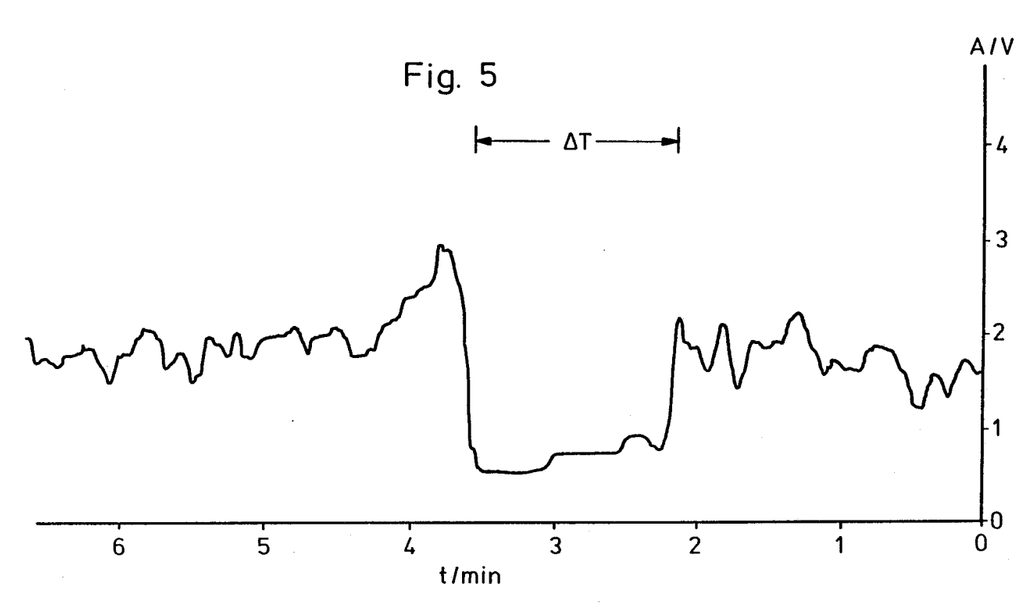
Figure 6:
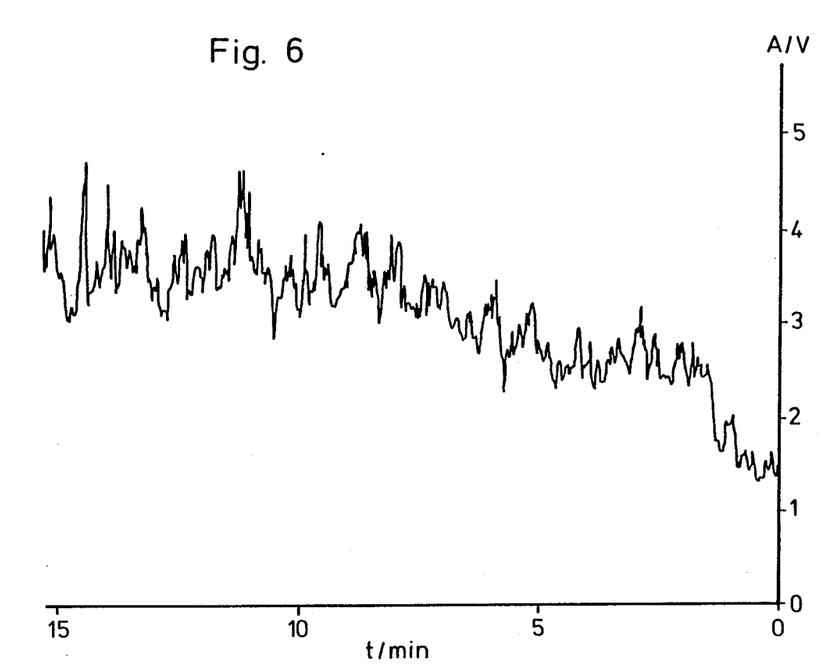

The time dependence of the flow of blood, with the blood supply suppressed during time interval $\Delta T$, is shown in FIG. 5 and the change in blood movement due to the use of a circulation enhancing ointment is shown in FIG. 6.

In practice, it may turn out to be appropriate to note that, in the determination of a value B indicating the flow of blood, other weightings bring about more easily distinguished or more stable measured values than the weightings discussed above. Weighting proportional to $v^2$ or $v^3$ would emphasize, in particular, the proportion of high velocities. Moreover, a step-type filter, a suitable highpass filter, which, on the one hand, suppresses the frequencies in the spectrum near zero, which are caused by the proportion of constant light in the speckle intensity, and, on the other hand, amplifies the remainder independently of frequency, can be used to generate a measured signal which indicates, for example, the amount of blood movement independently of velocity.

These weightings can be realized with a modified circuit arrangement. Amplification proportional to $v^2$ would correspond to twice performed differentiation, and amplification proportional to $v^3$ would require a special amplifier having such a characteristic. Filter 21 would then have to be more generalized to an element which amplifies the signal with specific frequency weighting.

Measurements made according to the method of the invention indicate that velocities up to several 100 microns per second can be detected. This lower limit is given by the available measuring aperture 30 of several microns in diameter, since in this way a minimum size is set for the speckles. To measure higher velocities, it is necessary to broaden the covered frequency range, so that the noise increases. This again can be compensated for by increasing the laser intensity.

For an exemplary embodiment of the invention see FIGS. 1 and 2. Specification of the components:
1: 7 mW HeNe-Laser, 633 nm
2: 80 mm focal-length lens
3: Optical fiber, diameter 0.3 mm
4: 16 mm focal-length lens
5: Diameter of the laser-spot 1.5 mm
7: Fiber bundle of 400 fibers with 70 $\mu$m diameter each
8: Fiber bundle leading to photocell 9
9: Silicon photocell with a sensitive area of $1.2 \times 1.2$ mm$^2$
10: Single fiber leading to the photomultiplier
11: Photomultiplier with a bialkali cathode
12: 633 nm interference filter
20: Amplifier with variable gain ($\approx 10$)
21: Differentiator with a characteristic frequency $f_d = 210$ Hz
22: Active high pass filter, 4-pole Butterworth, cut-off-frequency 50 Hz
24: 2% accuracy RMS/DC-Converter (Root-Mean-Square Processing)
25: Amplifier with variable gain ($\approx 100$)
26: 2% accuracy divider
28: Integratior with variable time-constants from 0.1 s to 4 s
30: Effective aperture for speckle-detection given by the diameter of one fiber: 70 $\mu$m
   Angle between beam 15 and axis 14: 15°
   Distance lens 4-aperture 30: 220 mm
   Distance lens 4-laser spot 5: 60 mm
23: Active lowpass filter, 4-pole Butterworth, cut-off-frequency 1500 Hz It will be understood that the above description of the present invention is susceptible to various modifications, changes and adaptations, and the same are intended to be comprehended within the meaning and range of equivalents of the appended claims.

What is claimed is:

1. A circuit for producing a representation of the velocity of an object in a given direction, which representation is proportional in amplitude to the velocity, by directing coherent radiation to the object in a direction substantially perpendicular to the given direction to produce a speckle pattern of radiation scattered from the object, the speckle pattern exhibiting a speckle spectrum which has, at a measuring location, a time dependency which is a function of movement of the object, said circuit comprising: first input means connected for producing a first signal representative of the instantaneous speckle intensity of the scattered radiation at the measuring location; second input means connected for producing a second signal representative of the average intensity of the scattered radiation at the measuring location; linear filter means connected to said first input means for linearly filtering the first signal; lowpass filter means connected to said linear filter means for receiving the linearly filtered first signal and passing only low frequency components of the first signal; RMS1DC-converter with first integrating means connected to said lowpass filter means for forming an integrated signal having a value representative of the integral of the low frequency components of the first signal; dividing means connected to receive the integrated signal from said first integrating means and to receive the second signal from said second input means for forming a signal representing the quotient of the value of the integrated signal divided by the value of the second signal; and second integrating means connected to said dividing means for forming an output signal representative of the time integral of the signal formed by said dividing means, which output signal corresponds to the representation of the velocity of the object.

2. A circuit as defined in claim 1 further comprising means connected to said dividing means for imparting an amplitude offset to the signal representing the quotient.

3. A circuit as defined in claim 2 further comprising highpass filter means selectively connectable in series between said linear filter means and said lowpass filter means.

4. A circuit as defined in claim 1 further comprising highpass filter means selectively connectable in series between said linear filter means and said lowpass filter means.

5. A circuit as defined in claim 1 constituting means for determining the velocity of blood flowing in living tissue independently of movement of the tissue.

6. A device for producing signals representative of the instantaneous speckle intensity and average intensity, at a measuring location, of a radiation speckle pattern produced by directing coherent radiation to an object from which the radiation is scattered to form the speckle pattern, comprising: a bundle of optical fibers, with one end of the bundle being arranged to be disposed at the measuring location; a first radiation detector connected to receive radiation from one of said fibers for producing the signal representative of the instantaneous speckle intensity; and a second radiation detector connected to receive radiation from all of the other fibers of said bundle for producing the signal representative of the average intensity.

7. A device as defined in claim 6 constituting means for determining the velocity of blood flowing in living tissue independently of movement of the tissue.

* * * * *